United States Patent
Matsumoto et al.

(10) Patent No.: US 9,784,754 B2
(45) Date of Patent: Oct. 10, 2017

(54) AUTOMATIC ANALYZER (71) Applicant: HITACHI HIGH-TECHNOLOGIES CORPORATION, Tokyo (JP)

(72) Inventors: Osamu Matsumoto, Tokyo (JP); Teruhiro Yamano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 62 days.

(21) Appl. No.: 14/437,974

(22) PCT Filed: Nov. 11, 2013

(86) PCT No.: PCT/JP2013/080444
§ 371 (c)(1),
(2) Date: Apr. 23, 2015

(87) PCT Pub. No.: WO2014/073684
PCT Pub. Date: May 15, 2014

(65) Prior Publication Data
US 2015/0293134 A1 Oct. 15, 2015

(30) Foreign Application Priority Data

Nov. 12, 2012 (JP) ................................ 2012-248005

(51) Int. Cl.
*G01N 35/00* (2006.01)
*G01N 35/10* (2006.01)

(52) U.S. Cl.
CPC ... *G01N 35/00623* (2013.01); *G01N 35/0092* (2013.01); *G01N 35/00663* (2013.01);
(Continued)

(58) Field of Classification Search
CPC ....... G01N 35/00623; G01N 35/00663; G01N 35/00712
See application file for complete search history.

(56) References Cited

U.S. PATENT DOCUMENTS

2008/0050280 A1* 2/2008 Fujita ............... G01N 35/00584
422/67
2013/0311243 A1 11/2013 Taki et al.

FOREIGN PATENT DOCUMENTS

EP 0359049 A2 3/1990
EP 1 892 531 A2 2/2008
(Continued)

OTHER PUBLICATIONS

Chinese Office Action received in corresponding Chinese Application No. 201380055333.8 dated Jan. 4, 2016.
(Continued)

*Primary Examiner* — P. Kathryn Wright
(74) *Attorney, Agent, or Firm* — Mattingly & Malur, PC (57) ABSTRACT

An automatic analyzer achieves both restraining unnecessary usage of a consumable supply and reducing burdens on an operator in a re-execution processing in a case where pipe functions are suspended/stopped, and is capable of completely efficiently performing an analysis preparation processing or an analysis terminating processing. In the automatic analyzer, a storage unit stores information on pipe functions, and information on re-execution setting for setting a re-execution maintenance item from which re-execution is started with respect to a suspended maintenance item if pipe functions of a plurality of maintenance items are suspended halfway, and a computer sequentially executes the plurality of maintenance items, based on the information on pipe functions, and re-executes maintenance from the re-execution maintenance item associated with a suspended maintenance item, based on the suspended maintenance item and the information on re-execution setting, if the pipe functions of the plurality of maintenance items are suspended halfway.

5 Claims, 10 Drawing Sheets

(52) U.S. Cl.
CPC .............. *G01N 35/00712* (2013.01); *G01N 2035/0094* (2013.01); *G01N 2035/00752* (2013.01)

(56) References Cited

FOREIGN PATENT DOCUMENTS

| | | |
|---|---|---|
| JP | 02-080962 A | 3/1990 |
| JP | 08-338846 A | 12/1996 |
| JP | 08-338847 A | 12/1996 |
| JP | 08-338848 A | 12/1996 |
| JP | 2012-018103 A | 1/2012 |
| WO | 2012/120755 A1 | 9/2012 |

OTHER PUBLICATIONS

Extended European Search Report received in corresponding European Application No. 13853667.7 dated Jun. 13, 2016.

\* cited by examiner

PIPE FUNCTION SETTING

| MAINTENANCE ITEM |
|---|
| PHOTOMETER CHECK |
| CELL BLANK MEASUREMENT |
| INCUBATION WATER EXCHANGE |
| AIR PURGE |
| WASH REACTION PARTS |
| REAGENT PRIME |
|  |
|  |

ADD >

<CANCEL

103a

| No | PIPE FUNCTION ITEMS | RE-EXECUTION SETTING |
|---|---|---|
| 1 | AIR PURGE | 1 ▶ |
| 2 | REAGENT PRIME | 1 ▶ |
| 3 | INCUBATION WATER EXCHANGE | 3 ▶ |
| 4 | CELL BLANK MEASUREMENT | 4 |
| 5 | PHOTOMETER CHECK | 4 |

1
2
3

REGISTER

DELETE

MAINTENANCE

| INTENDED PURPOSE |
|---|
| MAINTENANCE |
| CHECK |
| |
| |
| |
| |
| |
| |
| |

| MAINTENANCE ITEM | EXECUTION DATE AND TIME |
|---|---|
| PHOTOMETER CHECK | 2012/07/01 07:40:10 |
| CELL BLANK MEASUREMENT | 2012/07/02 07:30:15 |
| INCUBATION WATER EXCHANGE | 2012/07/02 07:15:35 |
| AIR PURGE | 2012/07/02 07:00:10 |
| WASH REACTION PARTS | 2012/07/01 18:59:00 |
| REAGENT PRIME | 2012/07/02 07:02:05 |
| | |
| | |
| | |

RE-EXECUTION OF PIPE FUNCTIONS ~201

EXECUTE

FIG. 10

PIPE FUNCTION SETTING

| 101 |
|---|
| MAINTENANCE ITEM |
| PHOTOMETER CHECK |
| CELL BLANK MEASUREMENT |
| INCUBATION WATER EXCHANGE |
| AIR PURGE |
| WASH REACTION PARTS |
| REAGENT PRIME |
| |
| |

ADD>

<CANCEL

| No | PIPE FUNCTION ITEMS 102 | RE-EXECUTION SETTING 103 | INTERRUPT ITEM 110 |
|---|---|---|---|
| 1 | AIR PURGE | 1 | RESET |
| 2 | REAGENT PRIME | 1 | – |
| 3 | INCUBATION WATER EXCHANGE | 3 | – |
| 4 | CELL BLANK MEASUREMENT | 4 | RESET |
| 5 | PHOTOMETER CHECK | 4 | – |

DELETE

REGISTER

FIG. 11

PIPE FUNCTION SETTING

| No | PIPE FUNCTION ITEMS 102 | RE-EXECUTION SETTING 103 | INTERRUPT ITEM DEPENDING ON CAUSE OF SUSPENSION 113 | |
|---|---|---|---|---|
| | | | MECHANICAL SYSTEM FAILURE 112 | CONSUMABLE SUPPLY SHORTAGE |
| 1 | AIR PURGE | 1 | RESET | – |
| 2 | REAGENT PRIME | 1 | – | REAGENT PRIME |
| 3 | INCUBATION WATER EXCHANGE | 3 | – | – |
| 4 | CELL BLANK MEASUREMENT | 4 | RESET | – |
| 5 | PHOTOMETER CHECK | 4 | – | – |

AUTOMATIC ANALYZER

TECHNICAL FIELD

The present invention relates to an automatic analyzer performing a qualitative/quantitative analysis of a biological sample, such as blood or urine, and in particular to a processing during suspension of an automatic analyzer provided with a function of automatically executing maintenance functions of the automatic analyzer.

BACKGROUND ART

An automatic analyzer performs, as daily maintenance, an analysis preparation processing performed when the analyzer is turned on or before an analysis is started, a rinse processing before the analyzer is turned off after an analysis terminates, and the like.

Further, there are many maintenance items associated with the analysis preparation processing and the rinse processing, and it takes time to perform such processing.

Therefore, regarding an automatic analyzer presetting an analysis preparation function performed when power is turned on or before an analysis is started, thereby performing a preparation function processing completely without waste, Japanese Patent Application Laid-Open No. H02-80962 (Patent Document 1) or Japanese Patent Application Laid-Open No. H08-338848 (Patent Document 2) proposes such an analyzer.

Further, Japanese Patent Application Laid-Open No. H08-338846 (Patent Document 3) proposes an automatic analyzer automatically executing an analysis termination processing before a power source of the analyzer is turned off.

Further, regarding a rinsing function before an analysis is started and when an analysis is terminated, Japanese Patent Application Laid-Open No. H08-338847 (Patent Document 4) proposes such a function.

Further, Japanese Patent Application Laid-Open No. 2012-018103 (Patent Document 5) proposes a system correctly calculating a maintenance duration time, thereby performing efficient maintenance.

RELATED ART DOCUMENTS

Patent Documents

Patent Document 1: Japanese Patent Application Laid-Open No. H02-80962
Patent Document 2: Japanese Patent Application Laid-Open No. H08-338848
Patent Document 3: Japanese Patent Application Laid-Open No. H08-338846
Patent Document 4: Japanese Patent Application Laid-Open No. H08-338847
Patent Document 5: Japanese Patent Application Laid-Open No. 2012-018103

SUMMARY OF THE INVENTION

Problems to be Solved by the Invention

By the way, while a plurality of maintenances are being executed in pipe functions sequentially automatically executing an analysis preparation processing or an analysis terminating processing described in the above patent document 1, a failure in a mechanical system may occur, or a consumable supply required for executing maintenance may become insufficient, and accordingly suspension/stop may occur without completing all maintenance items set as the pipe functions.

The automatic analyzers described in patent documents 2 to 5 may similarly be suspended/stopped during performance of a preparation function processing or maintenance, or the like.

Further, since a plurality of maintenance items may cooperate with each other to achieve an intended function so as to complete all maintenance items set as the pipe functions, it is also conceivable that simply re-executing a maintenance item(s) following a suspended maintenance item(s) may be insufficient.

Therefore, as a recovery processing in a case where the pipe functions are suspended/stopped, re-executing the pipe functions from the first, or causing an operator to confirm each maintenance item following a completed maintenance item(s) and designate and execute the maintenance items one by one is required.

However, if the pipe functions are re-executed from the start, a maintenance item(s) successfully completed is/are consequently repeated, and accordingly there has been a problem that a consumable supply for executing maintenance is unnecessarily consumed again, or maintenance time is wasted.

On the other hand, in a case where maintenance items are designated and executed one by one by an operator, operator's work takes a longer time, and accordingly decrease in efficiency is a problem.

Therefore, an object of the present invention is to provide an automatic analyzer achieving both restraining unnecessary usage of a consumable supply and reduction of burdens on an operator, and being capable of completely efficiently performing an analysis preparation processing or an analysis termination processing in a re-executing processing in a case where pipe functions are suspended/stopped.

The above described and other objects and novel features of the invention will be clear from the description of the specification and the accompanying drawings.

Means for Solving the Problems

Of the inventions disclosed in this application, the summary of the representative will be explained as below.

That is, the summary of the representative is to include an analyzing unit for analyzing a liquid sample; an input unit for inputting an analysis condition of the liquid sample; a display unit for displaying the inputted analysis condition; a storage unit for storing data analyzed in the analyzing unit and the analysis condition; and a control unit for controlling the analyzing unit, the input unit, the display unit, and the storage unit. The storage unit stores information on pipe functions for sequentially executing a plurality of maintenance items associated with a preparation processing performed before an analysis by the analyzing unit and a post-analysis processing performed after an analysis by the analyzing unit, and information on re-execution setting for setting a re-execution maintenance item from which re-execution is started with respect to the suspended maintenance item if the pipe functions of the plurality of maintenance items are suspended halfway, the information on pipe functions and the information on re-execution setting both being inputted from the input unit; and the control unit sequentially executes the plurality of maintenance items based on the information on the pipe functions, and re-executes maintenance from the re-execution maintenance item associated with the suspended maintenance item, based on the suspended maintenance item and the information on re-execution setting, if the pipe functions of the plurality of maintenance items are suspended.

Effects of the Invention

Among the inventions disclosed in the application, an advantageous effect obtained by the representative will be briefly explained as below.

That is, the advantageous effect obtained by the representative is that, even if the pipe functions are suspended halfway, only minimum essential maintenance items can be re-executed, so that efficient maintenance achieving both restraint of consumption of a consumable supply and shortening of maintenance time, and reduction of burdens on an operator can be executed.

BRIEF DESCRIPTIONS OF THE DRAWINGS

FIG. 10 is a diagram showing another setting example at the time of re-execution of pipe functions of an automatic analyzer according to an embodiment of the present invention.

DETAILED DESCRIPTION

Hereinafter, an embodiment of the present invention based on an outline of the embodiment will be described in detail with reference to the accompanying drawings. Note that components having the same function are denoted by the same reference symbols throughout the drawings for describing the embodiments, and the repetitive description thereof will be omitted.

<Configuration and Basic Functions of Automatic Analyzer>

Figure 1:
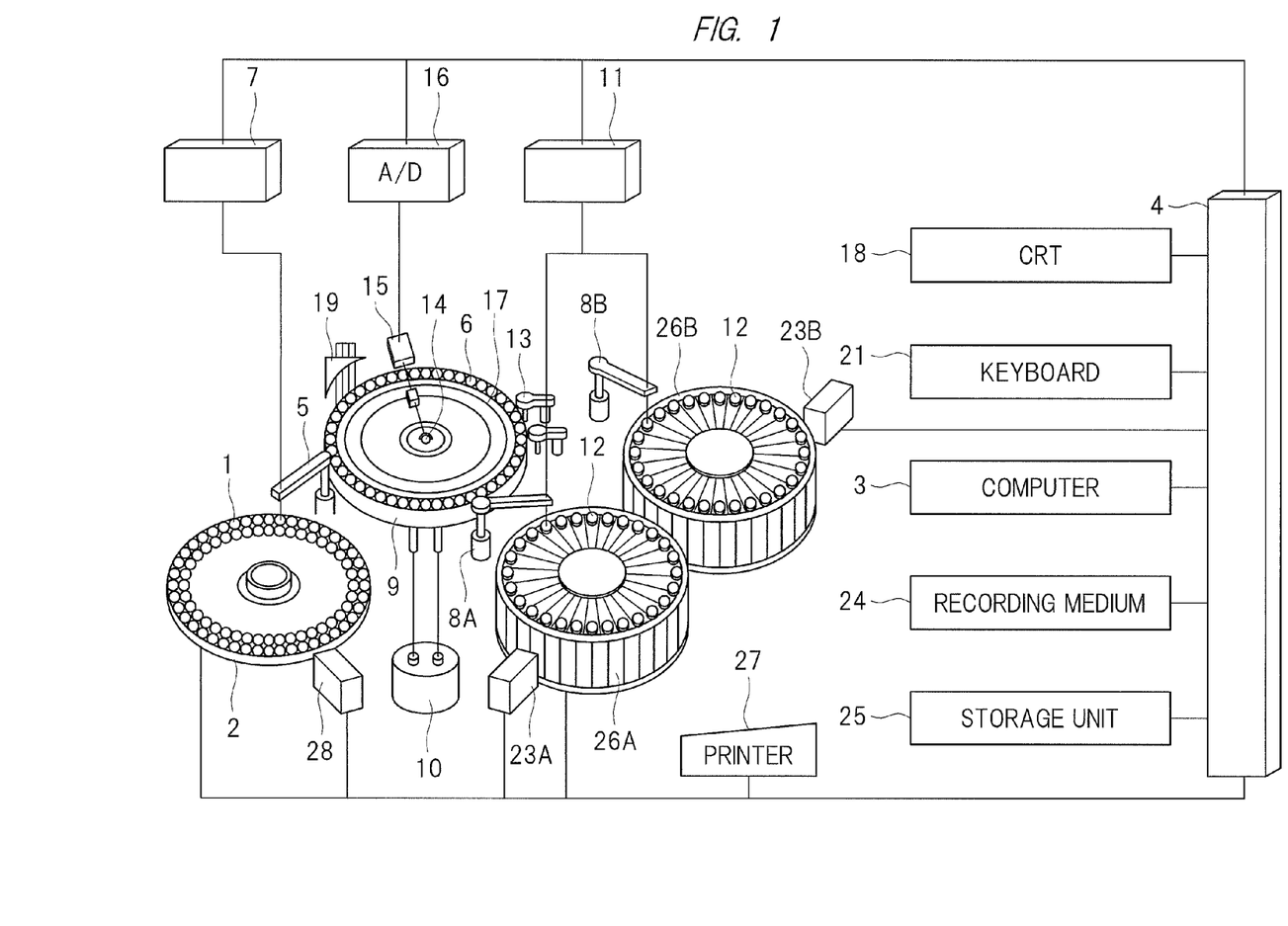
FIG. 1 is a configuration diagram showing a configuration of an automatic analyzer according to an embodiment of the present invention.
Figure 2:
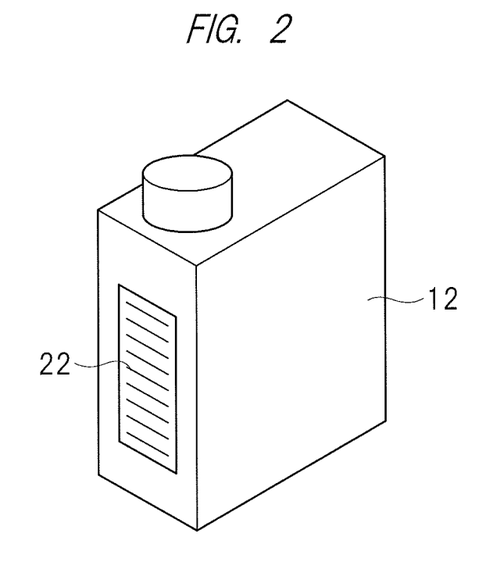
FIG. 2 is a diagram showing an example of a reagent bottle used in an automatic analyzer according to an embodiment of the present invention.
Figure 3:
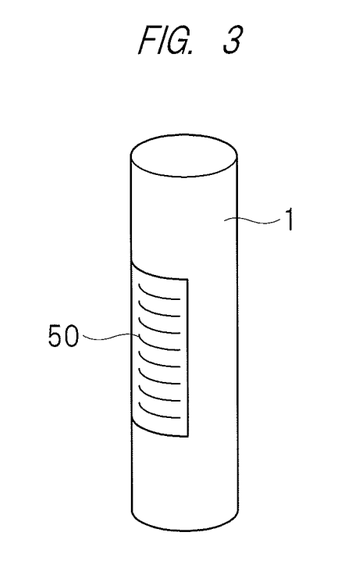
FIG. 3 is a diagram showing an example of a sample container used in an automatic analyzer according to an embodiment of the present invention.

With reference to FIG. 1 to FIG. 3, a configuration and basic functions of an automatic analyzer according to an embodiment of the present invention will be described. FIG. 1 is a configuration diagram showing a configuration of an automatic analyzer according to an embodiment of the present invention, FIG. 2 is a diagram showing an example of a reagent bottle used in an automatic analyzer according to an embodiment of the present invention, and FIG. 3 is a diagram showing an example of a sample container used in an automatic analyzer according to an embodiment of the present invention.

In FIG. 1, many sample containers 1 containing a sample, such as a liquid sample, are arranged on a sample disk 2. A supply drain nozzle of a sampling unit 5 is connected to a syringe pump for a sample 7.

Functions of the syringe pump for a sample 7 and the sampling unit 5 are controlled by a computer 3 that is a control unit performing function control of each unit and operations on measured data via an interface 4.

Many reaction containers 6 are arranged on a reaction table 17 rotatably provided to an incubation bath 9 to form a reaction line. Constant temperature liquid maintained at 37 degrees Celsius is supplied from a constant-temperature-liquid supplying unit 10 to the incubation bath 9.

A light source 14 and a multiwavelength spectroscope 15 are provided, and the reaction table 17 is rotationally transferred so as to cause a row of the reaction containers 6 to pass across a light beam from the light source 14. The reaction container 6 after use is rinsed by a rinsing unit 19 and provided for reuse.

A stirring unit 13 mixes a sample added in the reaction container 6 and reagent liquid associated with an analysis item of the sample with each other. A measurement signal based on reaction liquid obtained by the multiwavelength spectroscope 15 is converted from an analog signal to a digital signal by an A/D converter 16, and inputted into the computer 3.

On a reagent disk 26A for a first reagent and a reagent disk 26B for a second reagent, a variety of reagent bottles 12 associated with respective analysis items are circumferentially placed. That is, the reagent disks 26A and 26B are selectively-rotatable reagent bottle housing units.

A barcode reader 23A is provided in the vicinity of the reagent disk 26A, and the barcode reader 23B in the vicinity of the reagent disk 26B. A reagent pipetting instrument includes reagent pipettors 8A and 8B and a syringe pump for a reagent 11.

These reagent pipettors 8A and 8B suck and hold predetermined amounts of reagent liquids in the reagent bottles 12 stopped at sucking positions into supply drain nozzles, and these supply drain nozzles are turned to above the reaction container row, and reagent pipettors 8A and 8B discharge the reagent liquids held into the reaction containers 6 stopped at reagent receiving positions. The reagent liquids pipetted at this time are of kinds associated with analysis items assigned to respective reaction containers.

An analyzing unit includes the sample disk 2, the reaction container 6, the light source 14, the multiwavelength spectroscope 15, the reagent disk 26A for a first reagent, the reagent disk 26B for a second reagent, and other pipetting or rinsing configuration units.

Reagent barcode labels 22 having barcodes printed on the outer walls of the respective reagent bottles 12, as shown in FIG. 2, are attached to the reagent bottles 12.

Information which is displayed as this barcode is, for example, a reagent bottle code unique to each bottle composed of a sequence number, a size of the bottle, an expire date of the sample liquid, a reagent pipetting order indicating that the reagent is a first reagent, a second reagent or a third reagent, a maximum allowable number of analyses of the reagent liquid, a reagent pipetting amount showing a pipetting dose, a manufacturing lot number, and the like.

Further, the reagent information read by the barcode readers 23A and 23B from each reagent bottle 12 is stored in the storage unit 25 or each corresponding memory area of the computer 3.

Once the reagent bottles 12 are housed in the reagent disks 26A, and 26B, the reagent information is read by the barcode readers 23A and 23B, and at that time a signal indicating a set position of each reagent bottle is outputted by a rotation angle detecting unit provided in each sample disk, and inputted into the computer 3 via the interface 4. The reagent information and the bottle set position and the analysis item are stored so as to be associated with each other.

An operator can input various information using a screen of a CRT 18 that is a display unit and a keyboard 21 that is an input unit. A measurement result of an analysis item can be displayed on the printer 27 and the CRT 18. Information on a recording medium 24 is read by its reader, and stored in the storage unit 25 or an appropriate memory area of the computer 3.

Information stored in the storage 24, for example, includes the following: an analysis item code displayed in five digits; a parameter commonly used in the analysis item; a parameter stored individually for each reagent bottle; and the like.

Of them, the parameter commonly used in the analysis item includes a wavelength used in a photometer, a sample volume, a calibration method, a standard concentration, a number of standard liquids, an analysis-failure check limit value, and the like. Further, the parameter for each reagent bottle includes a reagent kind, a reagent pipetting order, a reagent bottle code, a reagent liquid volume, a reagent pipetting amount, a maximum allowable number of analyses, a reagent manufacturing date, and the like.

The storage 25 unit stores, in addition to the information read from the recording medium 24, an operation condition of each unit of the automatic analyzer, an analysis parameter of each analysis item, a determination logic performing management of each reagent bottle, a maximum allowable number of analyses read from a reagent bottle, an analysis result, and the like.

The reagent information is provided by the recording medium 24 provided by a manufacturer at the time of delivery of the reagent bottles. In a case where the reagent information is not prepared by the recording medium 24, the operator can also input information on a visual checking paper attached to the reagent bottle into the automatic analyzer via the screen and the keyboard 21.

A sample barcode label 50 having a barcode printed is attached to an outer wall of the sample container 1, as shown in FIG. 3. Information displayed as this barcode is, for example, a sample identification number uniquely identifying a sample.

This number is read by a barcode reader 28, and a correspondence between a sample position and the sample identification number is recognized according to angle detection of the sample disk 2.

On the other hand, an analysis item associated with the sample identification number is inputted and stored in advance via the keyboard 21 and the CRT 18, and consequently the sample position and the sample identification number and the analysis item are stored so as to be associated with each other at the previous barcode reading time. Further, whether the sample is a standard sample, a control sample or a general sample can be generally identified by an upper number of the sample identification number.

In an analysis of the entire automatic analyzer, as described below, sampling, reagent pipetting, stirring, photometry, rinsing of the reaction container, and data processing such as concentration conversion are conducted in this order.

A plurality of sample containers 1 containing a sample are placed on the sample disk 2. The sample disk 2 is controlled by the computer 3 via the interface 4. Further, the sample disk 2 causes the sample barcode label 50 on the outer wall of the sample container 1 to be read by the barcode reader 28, and the sample and the analysis item are associated with each other.

Thereafter, the sample containers 1 are rotationally moved to below a probe of the sampling unit 5 in the order of samples to be analyzed, and the sample in a predetermined sample container 1 is pipetted by a predetermined amount into the reaction container 6 by a function of the syringe pump for a sample 7 coupled to the sampling unit 5.

The reaction container 6 having the sample pipetted is moved to a first reagent adding position in the incubation bath 9. A reagent sucked from the reagent bottle 12 is added by a predetermined amount into the reaction container 6 that is moved by a function of the syringe pump for a reagent 11 coupled to the supply drain nozzle of the reagent pipettors 8A, 8B. The reaction container 6 after the first reagent addition is moved to a position of the stirring unit 13, where first stirring is performed.

In a case where a first reagent to a fourth reagent are set on the reagent disks 26A and 26B, addition to stirring of such a reagent is performed on each of the first to fourth reagents.

The reaction container 6 having the content stirred is caused to pass across a light flux emitted by the light source, and an absorbance at this time is detected by the multiwavelength spectroscope 15. A signal of the absorbance detected is inputted into the computer 3 via the interface 4 through the A/D converter 16, and converted into a sample concentration.

Data converted into concentration is outputted in a printing manner from the printer 27 via the interface 4, and displayed on the screen of the CRT 18. The reaction container 6 after photometry is moved to a position of the rinsing unit 19, rinsed with rinsing liquid after the content is discharged by a container washing pump, and provided for a next analysis.

<Maintenance Processing According to Pipe Function Setting>

Next, with reference to FIG. 4 to FIG. 6, a maintenance processing by pipe function setting of an automatic analyzer according to an embodiment of the present invention will be described.

Figure 4:
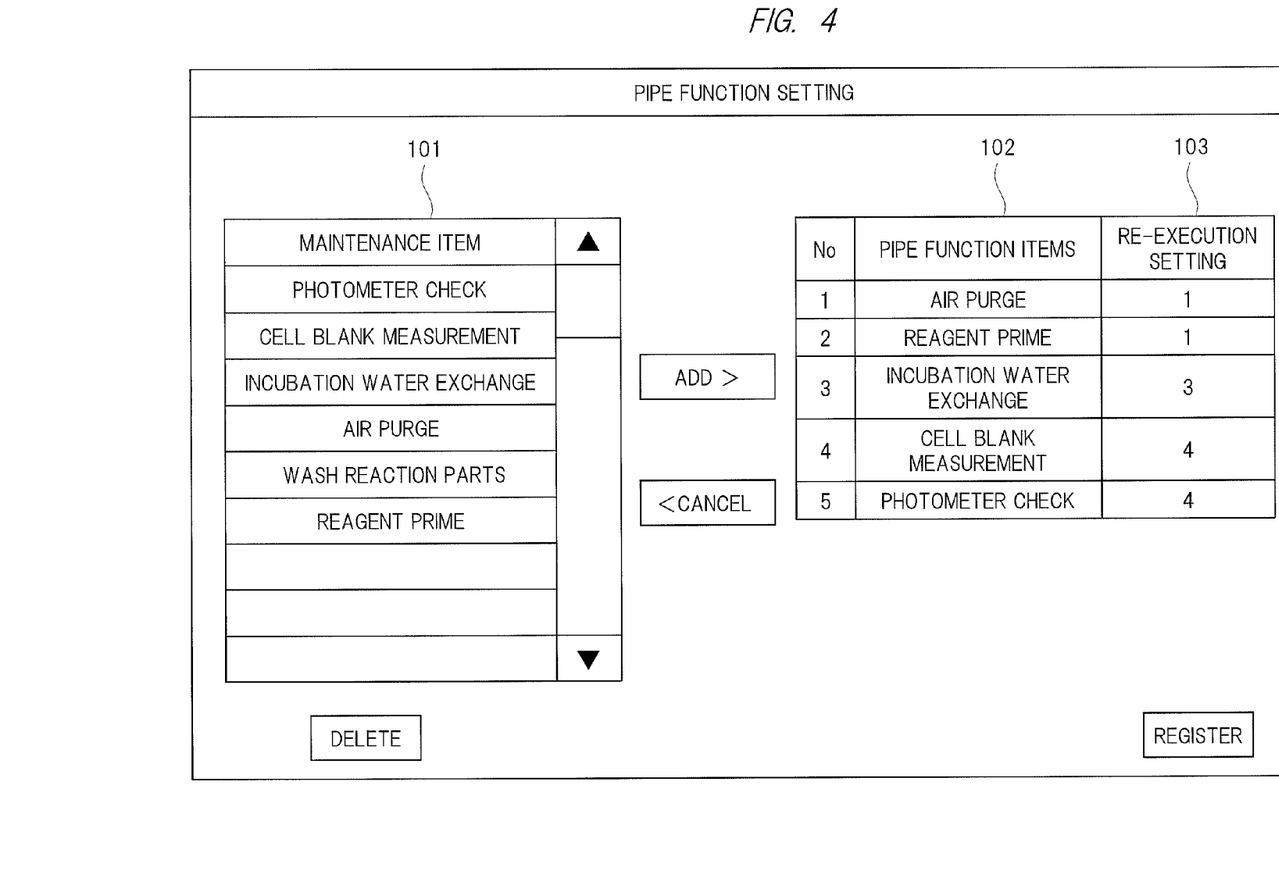
FIG. 4 is a diagram showing an example of a setting screen of pipe functions of an automatic analyzer according to an embodiment of the present invention.
Figure 5:
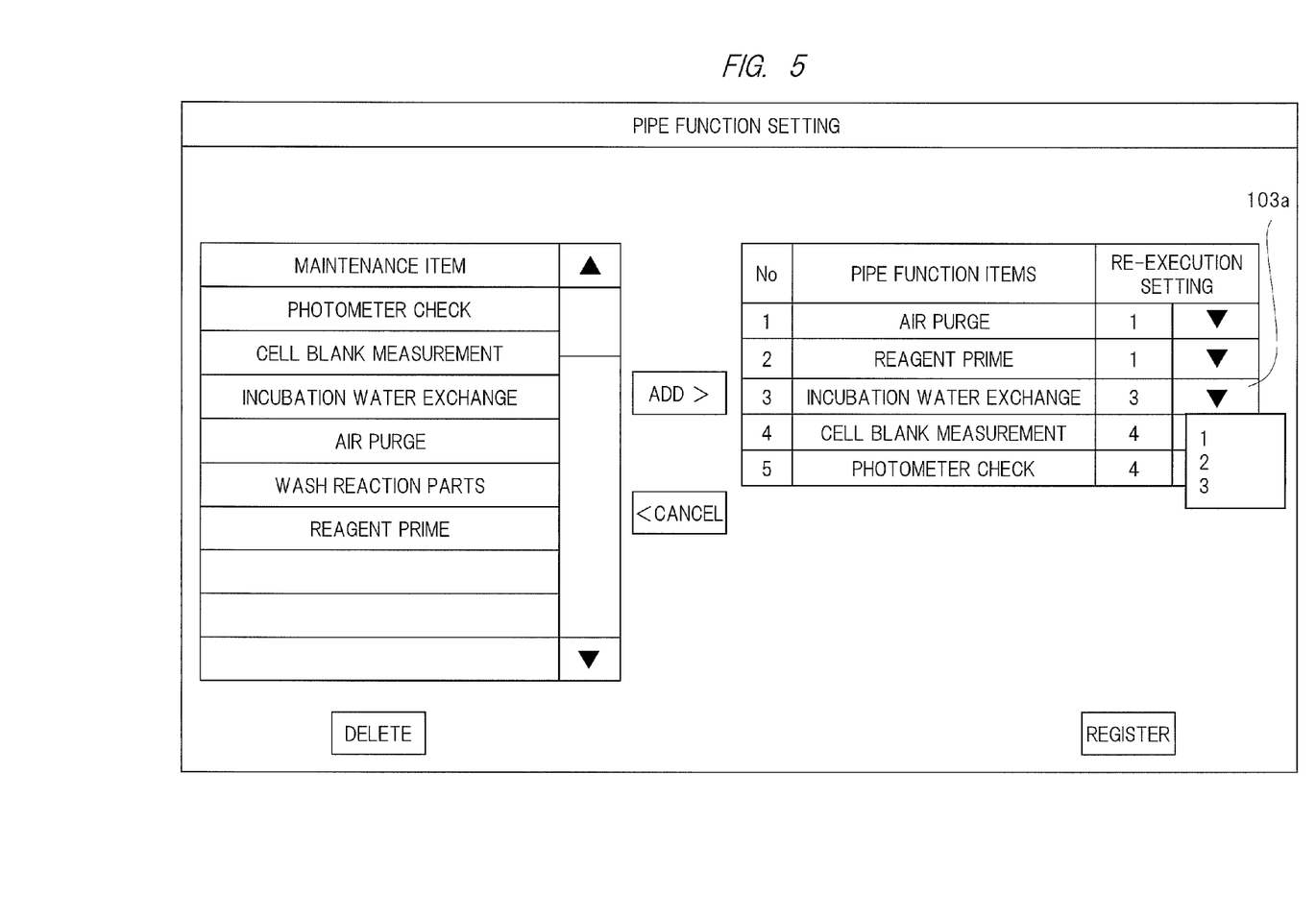
FIG. 5 is a diagram showing a set-value input example of a setting screen of pipe functions of an automatic analyzer according to an embodiment of the present invention.
Figure 6:
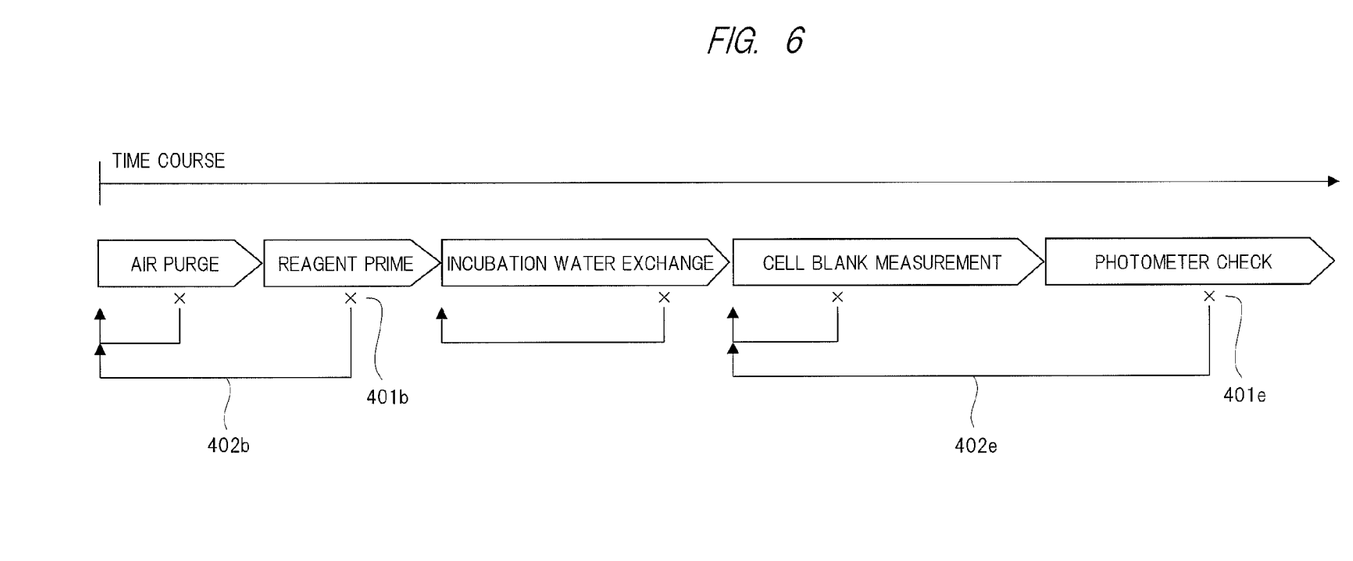
FIG. 6 is a function concept diagram in accordance with a time course of pipe functions and pipe function setting of an automatic analyzer according to an embodiment of the present invention.

FIG. 4 is a diagram showing an example of a setting screen of pipe functions of an automatic analyzer according to an embodiment of the present invention, FIG. 5 is a diagram showing a set-value input example of a setting screen of the pipe functions of an automatic analyzer according to an embodiment of the present invention, and FIG. 6 is a function concept diagram in accordance with a time course of the pipe functions and the pipe function setting of an automatic analyzer according to an embodiment of the present invention.

First, before maintenance is executed in the automatic analyzer, the operator sets a maintenance item from which re-execution starts if the pipe functions are suspended, for each maintenance item, on such a setting screen of pipe functions displayed on the screen of the CRT 18 by the computer 3 as shown in FIG. 4.

The setting screen of pipe functions, as shown in FIG. 4, displays a maintenance item list 102 selected as a pipe function item from a maintenance item list 101, and is provided with a re-execution setting input box 103 for setting a maintenance item from which re-execution starts at the time of re-execution of the pipe functions for each maintenance item that is selected.

According to information set on this setting screen of pipe functions, daily maintenance, such as a preparation processing performed when the automatic analyzer is turned on or before an analysis is started, or a post-analysis processing and a rinsing processing before the automatic analyzer is turned off after completion of an analysis, is performed.

In the case of the pipe function setting shown in FIG. 4, five maintenance items from No. 1 Air Purge to No. 5 Photometer Check included in the maintenance item list 102 are sequentially executed.

Air purge is maintenance for removing air bubbles inside a syringe tube of a pipettor used to suck/discharge liquid, such as a specimen sample or a reagent or a washing agent, and the air bubbles in a flow channel connected to the syringe tube. A pipettor is composed of the syringe tube, a plunger, and the like, and the syringe tube is filled with water. The plunger is driven by a motor so as to increase or decrease a volume of water in the syringe tube, thereby controlling a volume of water in the flow channel including a tube connected to the syringe tube. A probe is connected to a distal end of the tube, and, with the probe immersed in such liquid as a specimen sample or a reagent or a washing agent, the liquid is sucked by driving the plunger to suck. Further, after the probe is moved to a predetermined position, the liquid is discharged by driving the plunger to discharge. At this time, if an air bubble remains in the flow channel connected to the inside of the syringe tube, as compared with a case where the flow channel is filled with water, the volume of water in the flow channel cannot be well controlled by the sucking and discharging function of the plunger. Therefore, air purge for removing air bubbles in the flow channel is required for accuracy of liquid pipetting.

A maintenance item number may be inputted into the re-execution setting input box 103, as shown in FIG. 4, or a maintenance item number may be inputted therein with a select button 103*a*, as shown in FIG. 5.

A maintenance number to be inputted into the re-execution setting input box 103 shown in FIG. 4 is a maintenance number performed at the time of re-execution of the pipe functions if maintenance of the pipe function items is suspended.

In the case of the re-execution setting shown in FIG. 4, as shown in FIG. 6, during execution of the pipe functions, if a maintenance function stops 401*b* during execution of No. 2 Reagent Prime and then re-execution is instructed, the re-execution starts 402*b* from No. 1 Air Purge.

Similarly, if a maintenance function stops 401*e* during No. 5 Photometer Check, and then re-execution is instructed, the re-execution starts 402*e* from No. 4 Cell Blank Measurement.

<Re-Execution Processing in a Case where Pipe Functions are Suspended for Some Reason>

Figure 7:
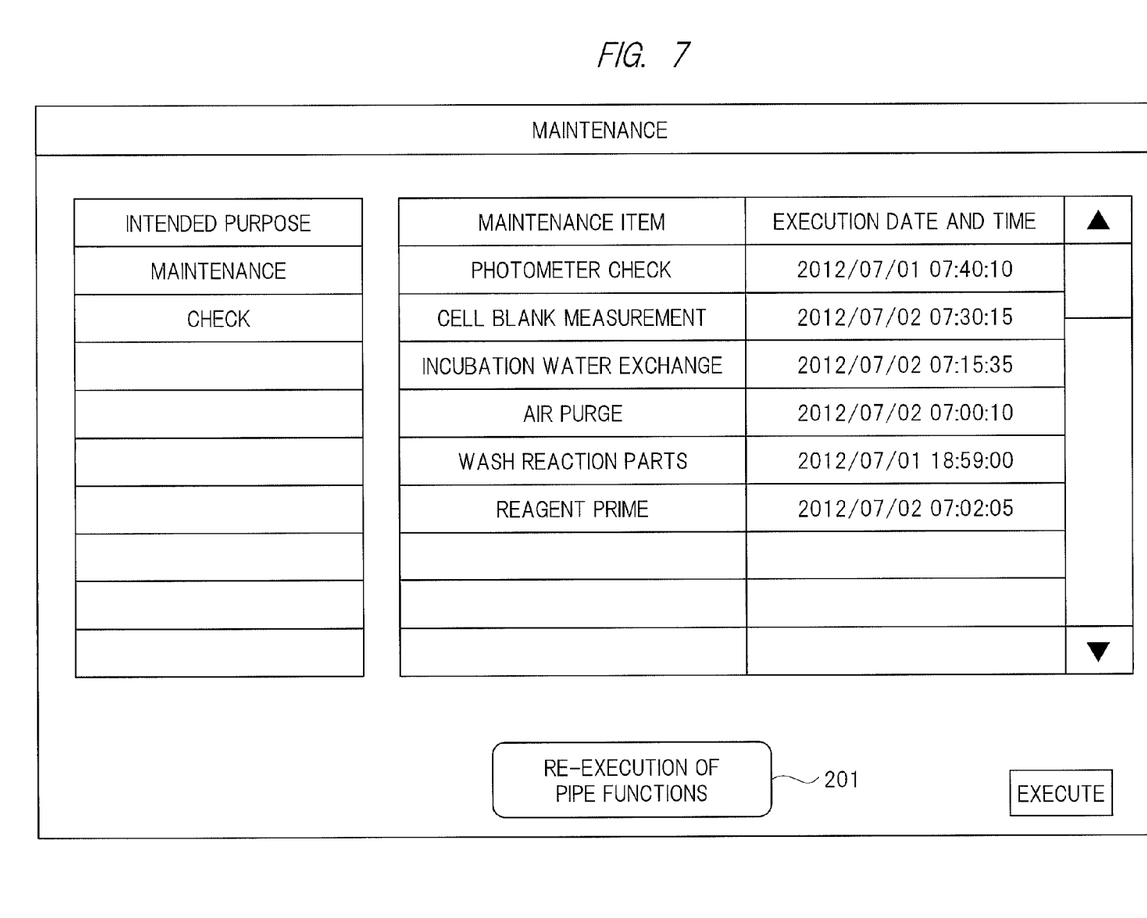
FIG. 7 is a diagram showing an example of an instruction screen for re-execution of pipe functions of an automatic analyzer according to an embodiment of the present invention.

Next, with reference to FIG. 7 to FIG. 9, a re-execution processing in a case where the pipe functions of an automatic analyzer are suspended for some reason according to an embodiment of the present invention will be described. FIG. 7 is a diagram showing an example of an instruction screen for re-execution of pipe functions of an automatic analyzer according to an embodiment of the present invention, FIG. 8 is a diagram showing a setting example at the time of re-execution of pipe functions of an automatic analyzer according to an embodiment of the present invention, and FIG. 9 is a flowchart showing a re-execution processing in a case where pipe functions of an automatic analyzer are suspended for some reason according to an embodiment of the present invention.

If pipe functions are suspended for some reason, the automatic analyzer stores the suspended maintenance item(s).

Then, the automatic analyzer displays the maintenance item and execution date and time, and the like, on such a maintenance screen displayed on the screen of the CRT 18 as shown in FIG. 7, and in a case where re-execution exactly as set in the re-execution setting of the pipe function setting shown in FIG. 4 is performed, the operator instructs re-execution of the pipe functions with a re-execution button of pipe functions 201 shown in FIG. 7.

Figure 8:
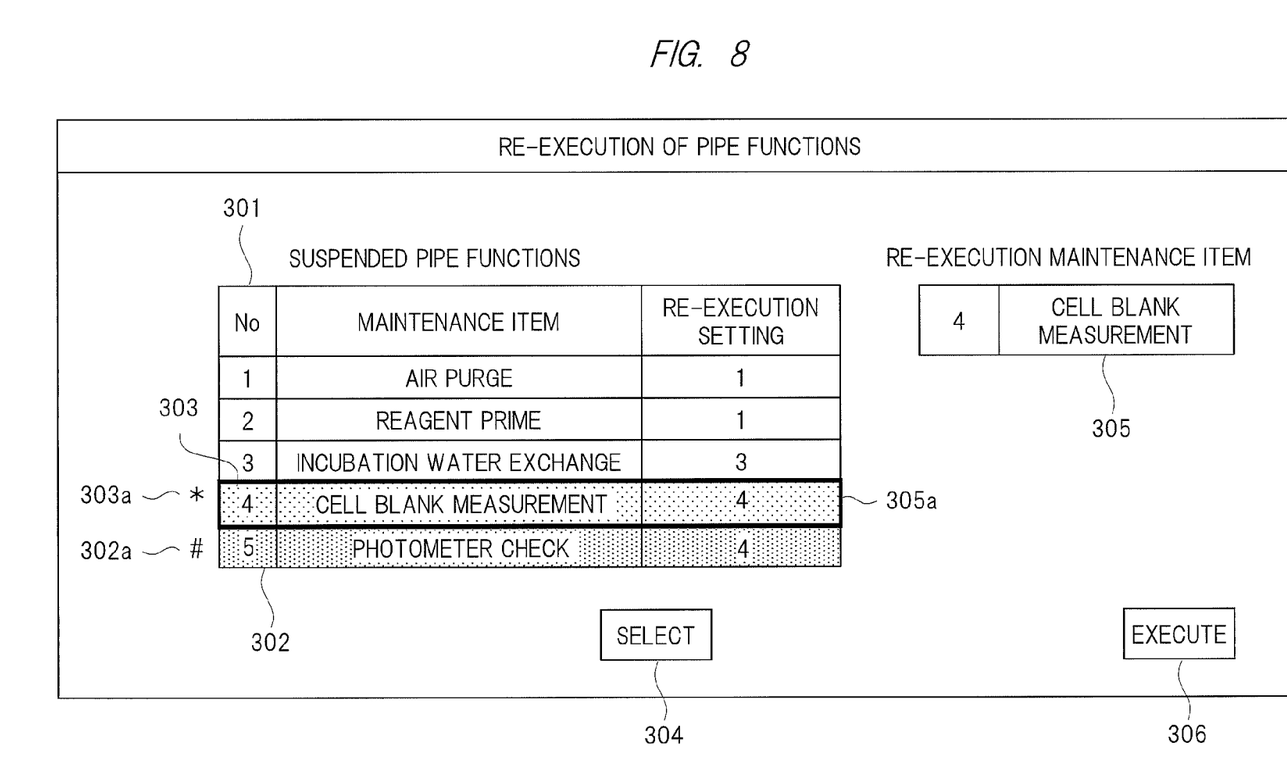
FIG. 8 is a diagram showing a setting example at the time of re-execution of pipe functions of an automatic analyzer according to an embodiment of the present invention.
Figure 9:
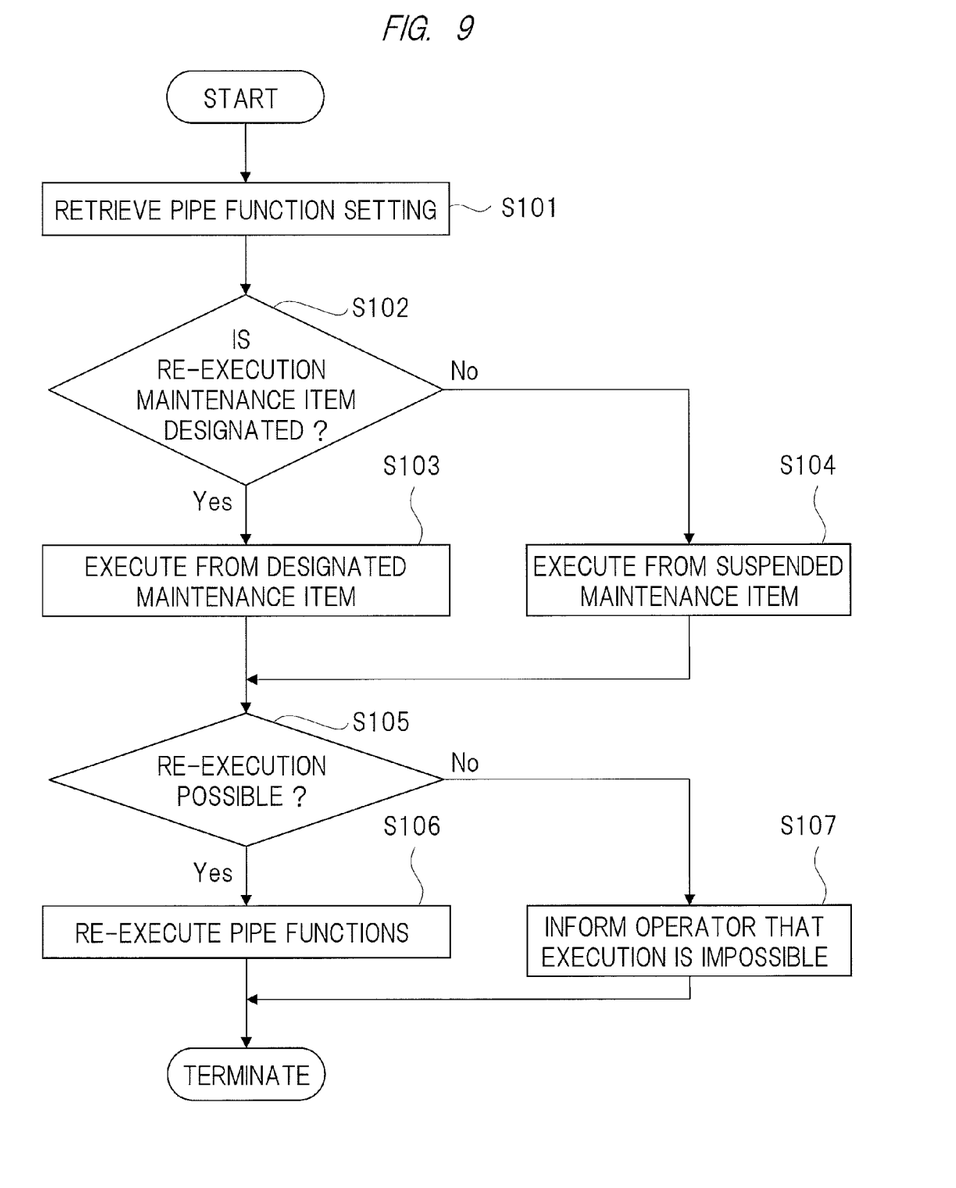
FIG. 9 is a flowchart showing a re-execution processing in a case where pipe functions of an automatic analyzer are suspended for some reason according to an embodiment of the present invention.

Alternatively, in a case where not re-execution exactly as set in the re-execution setting of the pipe function setting shown in FIG. 4 but re-execution started from an arbitrary maintenance item is performed at the time of re-execution of the suspended pipe functions, such a re-execution screen of the pipe functions as shown in FIG. 8 is displayed on the CRT 18.

The re-execution screen of the pipe functions displays in a list 301, maintenance items included in the suspended pipe functions, and has means 302 showing an operator a suspended maintenance item, and means 303 showing an operator a preset re-execution maintenance item.

The means 302 showing an operator a suspended maintenance item or the means 303 showing an operator a preset re-execution maintenance item may be displayed in special color, or a special mark 302*a*, 302*b* associated with each maintenance item may be additionally displayed.

The operator selects a maintenance item to be performed at the time of re-execution from the suspended maintenance item or the preset re-execution maintenance item, and makes the determination with the select button 304.

The selected re-execution maintenance item is displayed as a re-execution maintenance item 305 so as to be easily recognized by the operator. The display 305 of the selected re-execution maintenance item may be displayed in another display area, or may be displayed in a highlighting manner 305*a* on the maintenance item list 301.

A re-execution maintenance item is selected, and the pipe functions are re-executed from the selected maintenance item with an execution button 306.

Once the pipe functions are re-executed with the re-execution button of the pipe functions 201 shown in FIG. 7, or the execution button 306 shown in FIG. 8, as shown in FIG. 9, first, the stored suspended maintenance item is retrieved from the pipe function setting (step S101), and whether or not a re-execution maintenance item is designated is determined (step S102).

At step S102, for example, if a re-execution maintenance item is designated on such a re-execution screen of the pipe functions as shown in FIG. 8, it is determined that re-execution is performed from the designated maintenance item (step S103), or if a re-execution maintenance item is not designated at step S102, it is determined that re-execution is performed from the interrupted maintenance item (step S104).

Then, after completion of determination of a re-execution maintenance item at step S103 or step S104, whether or not re-execution is possible is determined based on judgment about a remaining amount of a consumable supply or a status of a mechanical system used for a maintenance item, following the re-execution maintenance item (step S105).

Then, if re-execution is possible at step S105, the pipe functions are re-executed (step S106), or if re-execution is not possible at step S105, the operator is informed that execution is impossible by means such as triggering a system alarm (step S107), and the processing is terminated.

<Another Setting Example of Pipe Function Setting>

Next, with reference to FIG. 10 and FIG. 11, other setting examples at the time of re-execution of pipe functions of an automatic analyzer according to an embodiment of the present invention will be described.

Figure 11:
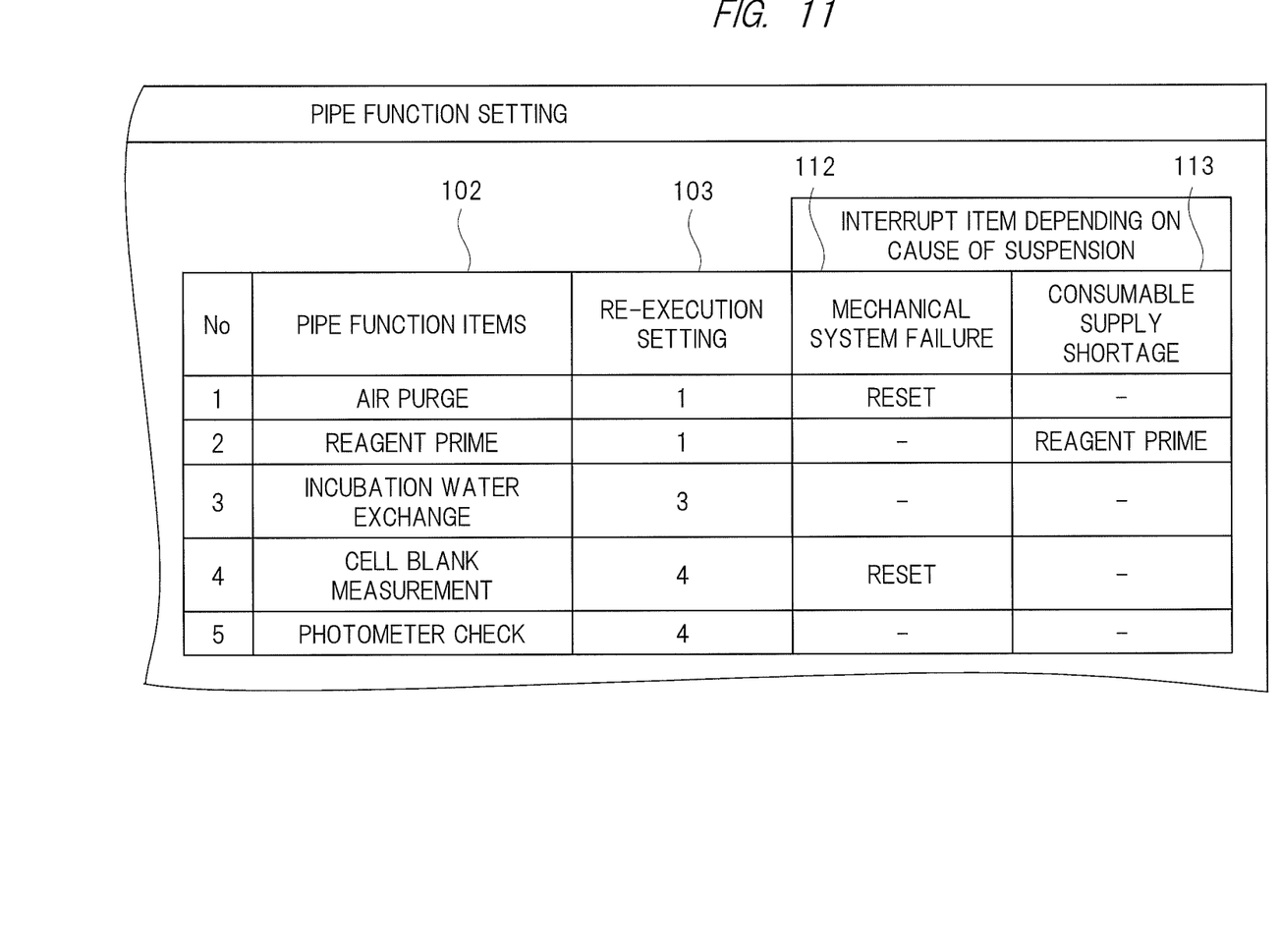
FIG. 11 is a diagram showing another setting example at the time of re-execution of pipe functions of an automatic analyzer according to an embodiment of the present invention.

FIG. 10 and FIG. 11 are diagrams showing other setting examples at the time of re-execution of pipe functions of an automatic analyzer according to an embodiment of the present invention. FIG. 10 is a setting example for performing interrupt execution of a maintenance item other than a maintenance item registered in pipe functions when the suspended pipe functions are re-executed, and FIG. 11 is a setting example for changing maintenance items to be interrupted depending on a cause of suspension and executing the maintenance items, when the pipe functions suspended are re-executed.

As shown in FIG. 10, as another setting example of a pipe function setting, for each maintenance item of the maintenance item list 102 registered as pipe functions, the re-execution setting input box 103 and an interrupt item input box 110 for a maintenance to be interrupted are provided.

By setting reset or the like in this interrupt item input box 110, a set maintenance item to be interrupted is performed at the time of re-execution of the pipe functions.

The setting example shown in FIG. 10 indicates that a reset function is executed before execution of air purge or before execution of cell blank measurement. The interrupt item input box 110 for maintenance to be interrupted may be a multiple-choice system for selecting a maintenance item name, a number associated with a maintenance item, or the like.

Reset of a maintenance item is a function of returning a position of each unit to an original position. Even when a mechanical system causes a function failure and stops during execution of maintenance, the units can be moved to proper positions by executing reset.

Further, in the setting in FIG. 10, air purge is performed as a first function of the pipe functions, and incubation water exchange is performed as a third function of the pipe functions. If no failure occurs during a series of pipe functions, incubation water exchange is performed soon after performance of air purge. In incubation water exchange, a hitargent solution is sucked from a reagent bottle and discharged into the incubation bath during maintenance, and therefore performing air purge in advance is beneficial. However, after completion of air purge of the pipe functions, if a failure occurs during incubation water exchange, consequently air purge and incubation water exchange are not sequentially performed and suspended. If time elapses in that state, the effect of air purge performed first is lost, pipetting and discharging of the hitargent solution may not be correctly performed. In order to solve this problem, air purge is set as an interrupt item with respect to the incubation water exchange in pipe function setting in FIG. 10. In the case of restart from incubation water exchange, air purge is executed before incubation water exchange, so that pipetting and discharging of the hitargent solution can be correctly performed.

Further, as shown in FIG. 11, another setting example of the pipe function setting, an area capable of setting an interrupt item depending on a cause of suspension associated with a plurality of causes of suspension is provided.

The setting example shown in FIG. 11 has two kinds of areas: a setting area 112 for a maintenance item to be executed when a cause of suspension is a function failure of a mechanical system; and a setting area 113 for a maintenance item to be executed in the event of a shortage of a consumable supply.

If the pipe functions are suspended because of a mechanical system failure, a reset function is executed before execution of air purge or before execution of cell blank measurement, and setting for a case where the pipe functions are suspended because of a shortage of a consumable supply indicates that reagent prime is executed as a maintenance item to be interrupted.

In the setting example shown in FIG. 11, setting is such that reagent prime is interrupted before reagent prime, so that reagent prime is executed twice. Reagent prime is a maintenance item for filling a reagent flow channel with the reagent, and the filling function is performed a plurality of times as a recovery processing responding to the occurrence of a shortage of the reagent during the filling. Thus, an effect of increasing reliability can be expected.

It should be noted that, in FIG. 11, two causes of suspension are described as an interrupt item depending on a cause of suspension, but causes of interruption may be classified into three or more, or a number capable of identifying a cause of suspension, such as an alarm number, may be used for the classification. Further, setting of suspension classification may be changeable, so that an operator may perform registration.

As described above, according to this embodiment, in the pipe function setting, since a re-execution maintenance item in a case where pipe functions are suspended/stopped is reset, and a re-execution processing is performed from the re-execution maintenance item that is set with respect to the suspended/stopped maintenance item, both restraining unnecessary usage of a consumable supply and reduction of burdens on an operator are achieved, so that an analysis preparation processing or an analysis terminating processing can be completely efficiently performed.

Further, by setting skip in the interrupt item box, if a maintenance item is stopped abnormally during pipe functions, it is also made possible to continuously execute a following maintenance item without suspension. Even when reagent prime is stopped because of a shortage of a consumable supply in the setting shown in FIG. 11, if setting is such that a following pipe function item is not affected by success and failure of a reagent prime function, it may be more efficient to continue pipe functions without suspension.

In the foregoing, the invention made by the inventors of the present invention has been concretely described based on the embodiments. However, it is needless to say that the present invention is not limited to the foregoing embodiments and various modifications and alterations can be made within the scope of the present invention.

REFERENCE SIGNS

1 . . . sample container, 2 . . . sample disk, 3 . . . computer, 4 . . . interface, 5 . . . sampling unit, 6 . . . reaction container, 7 . . . syringe pump for a sample, 8A, 8B . . . reagent pipettor, 9 . . . incubation bath, 10 . . . constant temperature liquid supplying unit, 11 . . . syringe pump for a reagent, 12 . . . reagent bottle, 13 . . . stirring unit, 14 . . . light source, 15 . . . multiwavelength spectroscope, 16 . . . A/D converter, 17 . . . reaction table, 18 . . . CRT, 19 . . . rinsing unit, 21 . . . keyboard, 22 . . . reagent barcode label, 23A, 23B . . . barcode reader, 24 . . . recording medium, 25 . . . storage unit, 26A, 26B . . . reagent disk, 27 . . . printer, 28 . . . barcode reader, 50 . . . sample barcode label, 101 . . . maintenance item list, 102 . . . maintenance item list selected as pipe function items, 103 . . . re-execution setting, 103a . . . multiple-choice type re-execution setting, 110 . . . setting of a maintenance item to be interrupted, 112 . . . setting of a maintenance item to be interrupted depending on a cause of suspension (cause of mechanical system failure), 113 . . . setting of a maintenance item to be interrupted depending on a cause of suspension (cause of consumable supply shortage), 201 . . . re-execution button of pipe functions, 301 . . . maintenance item list included in suspended pipe functions, 302 . . . example of displaying a suspended maintenance item in color, 302a . . . example of displaying a suspended maintenance item with a mark, 303 . . . example of displaying a preset re-execution maintenance item in color, 303a . . . example of displaying a preset re-execution maintenance item with a mark, 304 . . . re-execution maintenance select button, 305 . . . example of displaying a selected re-execution maintenance item in another area, 305a . . . example of displaying a re-execution maintenance item selected in a highlighting manner, 306 . . . re-execution button of pipe functions, 401b . . . stop during execution of reagent prime, 401e . . . stop during execution of photometer check, 402b . . . re-execution function after stop during execution of reagent prime, 402e . . . re-execution function after stop during execution of photometer check.

The invention claimed is:

1. An automatic analyzer comprising:
an analyzing unit for analyzing a liquid sample;
an input unit for inputting an analysis condition of the liquid sample;
a display unit for displaying the inputted analysis condition;
a storage unit for storing data, which are results of the analysis of the liquid sample analyzed by the analyzing unit, and the analysis condition; and
a control unit connected to the analyzing unit, the input unit, the display unit, and the storage unit,
wherein the storage unit stores information for executing a plurality of maintenance items, which are tasks performed by the automatic analyzer for maintenance of the automatic analyzer,
wherein the storage unit stores a sequential order of executing two or more of the plurality of maintenance items associated with a preparation processing performed before an analysis by the analyzing unit and a post-analysis processing performed after an analysis by the analyzing unit,
wherein the storage unit stores, for each of the two or more maintenance items, a re-execution value indicating a maintenance item, of the two or more maintenance items, from which re-execution of the preparation processing or the post-analysis processing begins according to the sequential order,
wherein the control unit is programmed to:
receive an input, via the input unit, for selecting the two or more maintenance items, of the plurality of maintenance items,
receive an input, via the input unit, for selecting the re-execution values for each of the selected two or more maintenance items,
execute the preparation processing by executing the two or more maintenance items according to the sequential order before an analysis of a liquid sample by the analysis unit,
execute the post-analysis processing by executing the two or more maintenance items according to the sequential order after the analysis of the liquid sample by the analyzing unit, and
if execution of a maintenance item, of the two or more maintenance items, is suspended during preparation processing or post-analysis processing, re-execute the preparation processing or the post-analysis processing according to the sequential order beginning at the maintenance item indicated by the re-execution value of the suspended maintenance item.

2. The automatic analyzer according to claim 1,
wherein the control unit is further programmed to:
display, on the display unit, the two or more maintenance items including the suspended maintenance item and the re-execution value corresponding to the two or more maintenance items,
receive an input, via the input unit, a selection of a maintenance item of the displayed two or more maintenance items, and
re-execute the preparation processing or the post-analysis processing according to the sequential order beginning at the selected maintenance item.

3. The automatic analyzer according to claim 1,
wherein the storage unit stores information of an interrupt item for each of the plurality of maintenance items, and
wherein the control unit is further programmed to perform a process associated with the interrupt item when the preparation processing or the post-analysis processing is re-executed after a maintenance item having the interrupt item is suspended.

4. The automatic analyzer according to claim 3,
wherein the interrupt item is associated with a plurality of causes of suspension for which a maintenance item is suspended, and
wherein the control unit is further programmed to select the interrupt item, based on the cause of suspension for which suspension has occurred, when the preparation processing or the post-analysis processing is re-executed.

5. The automatic analyzer according to claim 3,
wherein the process associated with the interrupt item is a reset function of resetting a component of the automatic analyzer to an initial position.

* * * * *